(12) United States Patent
Staats et al.

(10) Patent No.: US 7,991,451 B2
(45) Date of Patent: *Aug. 2, 2011

(54) METHOD OF OPERATION FOR A MAGNETIC RESONANCE IMAGING SUITE

(75) Inventors: Peter Staats, Loveland, OH (US); James A. Knipfer, II, Ft. Wright, KY (US)

(73) Assignee: Liebel-Flarsheim Co., Cincinnati, OH (US)

( * ) Notice: Subject to any disclaimer, the term of this patent is extended or adjusted under 35 U.S.C. 154(b) by 459 days.

This patent is subject to a terminal disclaimer.

(21) Appl. No.: 11/938,553

(22) Filed: Nov. 12, 2007

(65) Prior Publication Data

US 2008/0068011 A1 Mar. 20, 2008

Related U.S. Application Data

(63) Continuation of application No. 09/851,462, filed on May 8, 2001, now Pat. No. 7,512,434.

(51) Int. Cl.
*A61B 5/055* (2006.01)
*A61B 6/00* (2006.01)
*G01V 3/00* (2006.01)

(52) U.S. Cl. ......... 600/420; 324/307; 600/431

(58) Field of Classification Search .......... 600/420, 600/431; 324/307, 309, 318; 604/131
See application file for complete search history.

(56) References Cited

U.S. PATENT DOCUMENTS

| | | | |
|---|---|---|---|
| 4,613,820 A | 9/1986 | Edelstein et al. | |
| 5,432,544 A | 7/1995 | Ziarati | |
| 5,592,030 A * | 1/1997 | Adahan | 307/80 |
| 5,877,732 A | 3/1999 | Ziarati | |
| RE36,648 E | 4/2000 | Uber, III et al. | |
| 6,198,285 B1 | 3/2001 | Kormos et al. | |
| 6,590,391 B1 | 7/2003 | Shudo et al. | |
| 6,675,037 B1 * | 1/2004 | Tsekos | 600/417 |
| 6,845,262 B2 | 1/2005 | Albert et al. | |
| 6,882,785 B2 | 4/2005 | Eichelberger et al. | |
| 7,267,661 B2 * | 9/2007 | Susi | 604/67 |
| 7,343,191 B1 | 3/2008 | Damadian et al. | |

(Continued)

FOREIGN PATENT DOCUMENTS

EP 655220 A1 5/1995

(Continued)

OTHER PUBLICATIONS

Saini, et al., "In Vitro Evaluation of a Mechanical Injector for Infusion of Magnetic Resonance Contrast Media", Investigative Radiology, vol. 26, No. 8, Aug. 1991, pp. 748-751.

(Continued)

*Primary Examiner* — Michael T Rozanski
(74) *Attorney, Agent, or Firm* — Wood, Herron & Evans, LLP

(57) ABSTRACT

A method of operation for a magnetic resonance imaging suite. A power supply of magnetic resonance injector system receives electrical power from an AC power outlet, both of which are located outside of a shielded room of the magnetic resonance imaging suite. Electrical power from the power supply of the magnetic resonance injector system is conveyed (via an appropriate power connection) into the shielded room of the magnetic resonance imaging suite and to a component (e.g., a power head) of the magnetic resonance injector system located inside the shielded room. While this electrical power is being conveyed, radio frequency energy emitted from the power connection is being filtered.

18 Claims, 2 Drawing Sheets

U.S. PATENT DOCUMENTS

| | | |
|---|---|---|
| 7,512,434 B2 | 3/2009 | Staats et al. |
| 2001/0037063 A1 | 11/2001 | Albert et al. |
| 2002/0169415 A1 | 11/2002 | Staats et al. |
| 2003/0050555 A1 | 3/2003 | Critchlow et al. |
| 2004/0197058 A1 | 10/2004 | Eichelberger et al. |
| 2005/0273000 A1 | 12/2005 | Dinehart et al. |
| 2007/0285021 A1 | 12/2007 | Jauster et al. |
| 2008/0068011 A1 | 3/2008 | Staats et al. |
| 2009/0045812 A1 | 2/2009 | Staats et al. |

FOREIGN PATENT DOCUMENTS

| | | |
|---|---|---|
| JP | 8-2100970 | 8/1996 |
| JP | 9-289983 A | 11/1997 |
| WO | 00-74752 A1 | 12/2000 |

OTHER PUBLICATIONS

European Patent Office, International Search Report issued in corresponding PCT Application serial No. PCT/US2002/13282 dated Aug. 28, 2002.

Mallinckrodt Service and Parts Manual "Optistar MR Digital Injection System", Mar. 2000 (155 pages).

Japanese Abstract; Power System for Computer and Its Control Method; JP8-211970, Sun Microsystems, Inc., Aug. 20, 1996.

Brummett et al., "Power Injectors for MRI", Applied Radiology, May 1999.

Nintendo GAME BOY Rechargeable Battery Pack / AC Adaptor Owner's Manual (1989).

Sony Digital Video Camera Recorder Operating Instructions for the DCR-TRV120/TRV320 (2000).

Aiwa XP-R100 Operating Instructions (undated).

Nokia 5160/5160i Owner's Manual (1999-2001).

Hewlett-Packard HP-25 Owner's Handbook (1975).

3Com Handbook for the Palm V Organizer (1998-1999).

Leland H. Hemming, "Architectural electromagnetic Shielding Handbook, A Design and specification Guide", IEEE Press (1991), p. 131.

Walter Scott Reg. No. 30,588, Request for Reexamination for Patent No. 7512434 issued Mar. 31, 2009, filed with US Patent Office Dec. 21, 2009.

Walter Scott, Citation of Prior Art under 37 CFR 1.501 and 1449, Filed Dec. 10, 2009, 5 pages.

JP 9-289983 Abstract, Open Type Magnetic Resonance Imaging Device, (1997).

* cited by examiner

METHOD OF OPERATION FOR A MAGNETIC RESONANCE IMAGING SUITE

CROSS REFERENCE TO RELATED APPLICATIONS

This application is a continuation of U.S. patent application Ser. No. 09/851,462 filed on 8 May 2001 now U.S. Pat. No. 7,512,434 and entitled "Remotely Powered MR Injector", the disclosure of which is hereby incorporated by reference.

FIELD OF THE INVENTION

The invention relates to contrast media power injectors compatible for use within a magnetic resonance imaging (MRI) suite, and in particular, to electrical interconnection of components of a magnetic resonance (MR) injector.

BACKGROUND

A Magnetic Resonance Imaging (MRI) unit consists of a large cylindrical superconducting magnet for generating a strong magnetic field, devices for transmitting and receiving radio waves, and a complex computer system. When a patient lies inside the MRI unit, the strong magnetic field causes the hydrogen nuclei in the patient to line up. A low-frequency radio wave is pulsed through the magnet into the patient. The hydrogen atoms absorb the energy released by the radio waves. This disrupts the uniformity of the nuclei. When the radio-wave stimulation stops, the nuclei return to their original state and emit energy in the form of weak radio frequency (RF) signals. The strength and length of these RF signals— and therefore the kind of image produced—depend on the properties of the organ or tissue involved. A computer translates the RF signals into highly detailed cross-sectional images. The images are essentially maps of the locations of water or hydrogen in the body. The magnetic field produced by the MRI unit constrains installation of associated MRI equipment. In particular, any ferromagnetic object near the MRI unit will be attracted by the magnetic field, either impairing operation of the equipment or becoming a safety hazard if forcibly projected toward the MRI unit. Also, the uniformity of the magnetic field of the MRI unit is altered by ferromagnetic material, even if the ferromagnetic material is secured to prevent safety hazards. Consequently, ferromagnetic material is generally kept away from the MRI unit.

The radio frequency transmissions emitted by the MRI unit toward the patient also poses electromagnetic interference/compatibility (EMIC) constraints on the installation of other equipment. General consumer and medical equipment such as personal computers and monitors are typically inadequately shielded to prevent impairment of function due to the strength of such RF emissions. Inversely, the MRI unit is susceptible to degraded performance if RF noise from other equipment distorts the received RF signal during imaging.

For these reasons, the core of the MRI unit, including the magnetic field producing and RF transmission and receiving portions, is placed within a magnet room that is shielded from the other rooms of the MRI suite and the rest of the facility. Often, nonferrous metal sheets or mesh encompass the entire magnet room to prevent magnetic energy and RF energy from entering or leaving the magnet room. Consequently, the MRI unit generally includes highly shielded electrical power, data and control cabling that are routed through filtered and grounded access points so that susceptible or interfering components of the MRI unit may be placed outside of the shielded room.

The same installation constraints affect installation of other equipment in the shielded magnet room. For example, utility electrical power, typically provided as AC outlets throughout the facility, is a transmission path for RF noise and is thus often not provided in the shielded magnet room. Similarly, sensors and controls for equipment used in the MRI suite often have to be placed in another room of the MRI suite, typically either an equipment room or control room. These controls are connected to the magnet room via a penetration panel that maintains the EMI shielding while allowing penetration by shielded and filtered electrical cables.

As MRI units became capable of increased computational speed, opportunities were presented for use of contrast media, injected into patients before or during an MRI scan, to enhance dynamic imaging studies. In addition, contrast media were developed that allowed MRI scanning of certain types of tissues that otherwise were insufficiently distinguishable from surrounding tissue for effective MRI diagnostic studies. Power injectors for contrast media are sometimes preferred due to repeatability of dosage volumes and injection rates and keeping personnel away from the MRI unit during a scan. However, adapting contrast media injectors from other radiological modalities (e.g., X-ray, Computer-aided Tomography (CT), etc.) was difficult due to MRI unit installation limitations.

With reference to FIG. 1, a power injector system 10 for injecting image-enhancing contrast media into a patient before or during an MRI scan is depicted as installed in an MRI suite 12. In particular, the power injector system 10 depicted is an OPTISTAR™ magnetic resonance (MR) digital injection system available from Mallinckrodt, Liebel-Flarsheim Business, Cincinnati, Ohio. The system 10 successfully operates within an MRI suite 12 by placement of components at varying distances from an MRI unit 14 or with varying degrees of shielding. In particular, a power head 16 contains ultrasonic motors. The ultrasonic motors operate syringes to dispense contrast media and saline solution into a patient as commanded and powered over a shielded power head cable 18 by a power control 20.

The power control 20 is also within a shielded magnet room 22 of the MRI suite 12 along with the power head 16 and the MRI unit 14, although generally spaced away from the MRI unit 14 to reduce the EMIC considerations. Since AC outlets are generally not available in the shielded magnet room 22, the power control 20 is battery powered. The power control 20 provides power to the power head 16 in response to data signals that are relayed from the power head 16 to the power control 20 and between the power control 20 and a touch-screen console 24 outside of the shielded magnet room 22. In particular, a shielded electrical cable 26 for transferring data signals couples the power control 20 to an opening, such as a free hanging D-shell connector 28, in a penetration panel 30. An electrical cable 32 outside of the shielded magnet room 22 is electrically coupled to the other electrical cable 26 inside the shielded magnet room 22 via a filter 34 connected to the penetration panel 30. The filter 34 reduces RF noise induced on the cables 26, 32. In the depicted MRI suite 12, the cable 32 passes from an equipment room 36 that is positioned adjacent to the penetration panel 30 to a control room 38 where the MRI unit controls (not shown) and the power injector touch-screen console 24 reside.

Since the power control 20, and thus the power head 16, is battery powered, a battery charger 40 is placed in the control room 38 for recharging a battery 42 for use in the power control 20. The battery charger 40 receives its power from an AC outlet 44. Thus, an inconvenient task is placed on operators of the MRI unit 14 and battery-powered injector system 10 to monitor the state of charge of batteries 42 and swap batteries between the battery charger 40 and the power control 20. If an undercharge of batteries 42 installed in the power control 20 is not detected in a timely fashion, the operation of the MRI unit 14 is delayed, reducing the number of patients that may be scanned. Such reduction in the number of patients increases medical costs and limits delivery of medical services.

In addition to clinical and staffing considerations, there is the increased inventory of batteries 42 necessary to have sufficient batteries for both use and simultaneous recharging. Furthermore, use of battery power places design constraints upon the battery-powered injector system 10, such as reducing functionality or increasing the size and cost of the batteries 42 to handle the power demand.

As an example of a design constraint, the power control 20 provides power for the electronic components and the ultrasonic motors of the power head 16 and the electronic components of the power control 20 itself. The power control 20 does not power components outside the magnet room 22. Consequently, several of the major components of the battery-powered injector system 10 each individually have internal power supplies that regulate and convert electrical power for use by that major component. For example, the console includes a power supply that also receives power from the AC outlet 44 and converts the AC electrical power to DC voltages useful for the electronics and display devices therein. Similarly, the battery charger 40 includes an internal power supply that regulates and converts AC power to voltages suitable for its electronics and for the battery 42 being recharged. Also, the power control 20 includes an internal power supply for regulating and converting the battery power from installed batteries 42 for the voltages required for its operation. Each internal power supply increases the cost, the size, and the cooling requirement of each major component.

Therefore, a significant need exists for an MR injector system with reduced cost that is simpler to operate than current battery-powered injector systems.

SUMMARY

The present invention addresses these problems with a remotely powered MR injector that efficiently utilizes AC electrical power provided at convenient AC outlets in a control room of an MRI suite. In particular, a remotely positioned power supply supplies the electrical power requirements for the entire MR injector system. Operators are no longer inconvenienced by charging and replacing batteries. In addition, installation of the MR injector system is enhanced by incorporating electrical power transmission into shielded electrical cables that also transmit data signals.

In one particular aspect of the present invention, a power supply outside of the shielded magnet room provides electrical power to a power head inside of the shielded magnet room via electrical cables coupled through a penetration panel.

In another aspect of the present invention, the power supply replaces a battery charger in an existing battery-powered injector system by providing electrical power across the penetration panel to a power control inside the shielded magnet room. The power control actuates a power head, which is near an MRI unit, to inject contrast agent and saline into patients undergoing an MRI scan. In particular, electrical power from an electrical cable from the penetration panel is interconnected with internal conductors of the power control that previously received power from a battery. The power supply is thus configured to provide electrical power equivalent to those of previously-used batteries. Thereby, existing MR injector systems receive many of the benefits provided by a remotely powered MR injector system.

The above and other objects and advantages of the present invention shall be made apparent from the accompanying figures and the description thereof.

BRIEF DESCRIPTION OF THE FIGURES

The accompanying figures, which are incorporated in and constitute a part of this specification, illustrate embodiments of the invention and, together with a general description of the invention given above, and the detailed description of the embodiments given below, serve to explain the principles of the invention.

DETAILED DESCRIPTION OF SPECIFIC EMBODIMENTS

Figure 1:
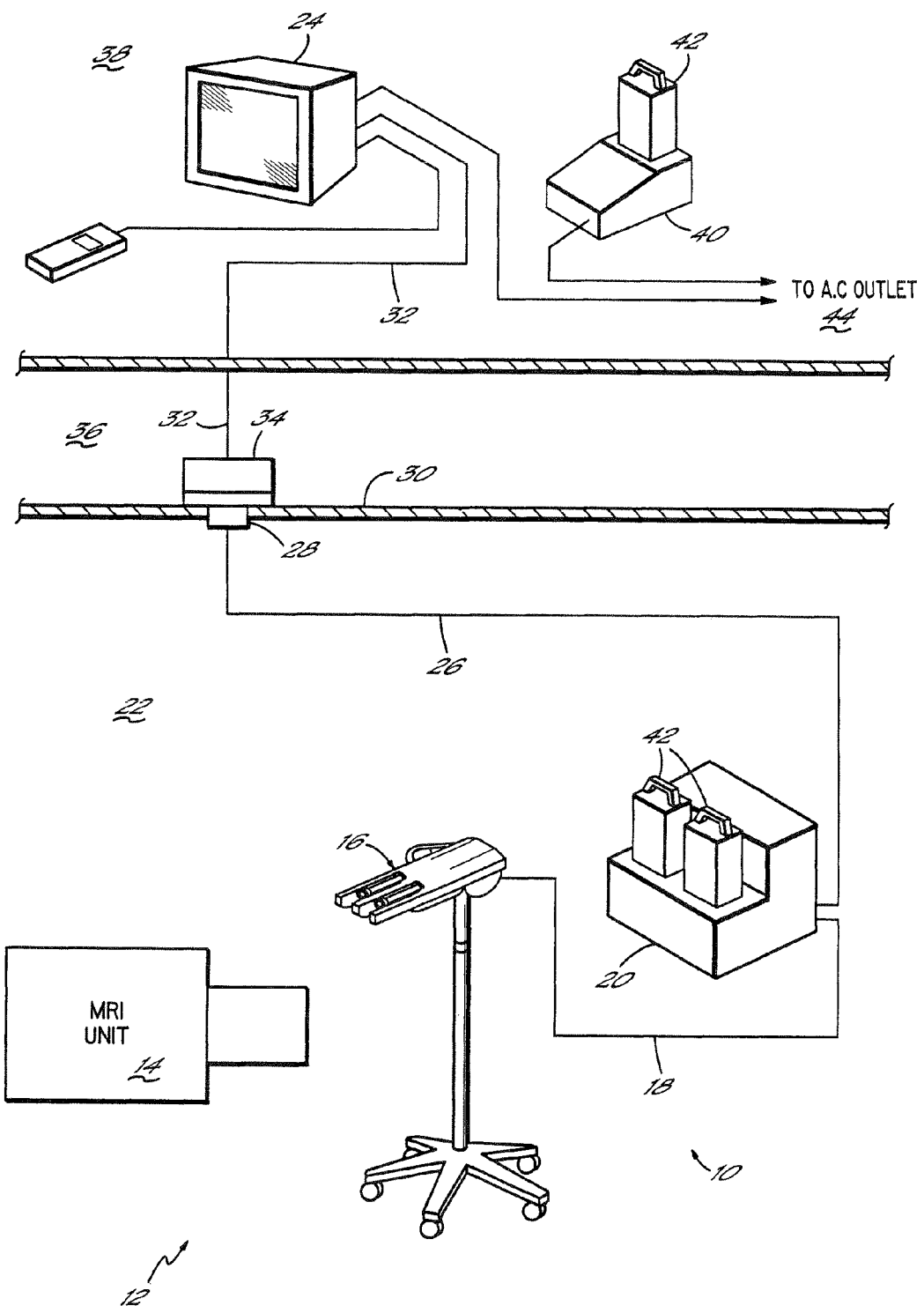
FIG. 1 is schematic of a prior art battery-powered injector installed in a magnetic resonance imaging (MRI) suite.
Figure 2:
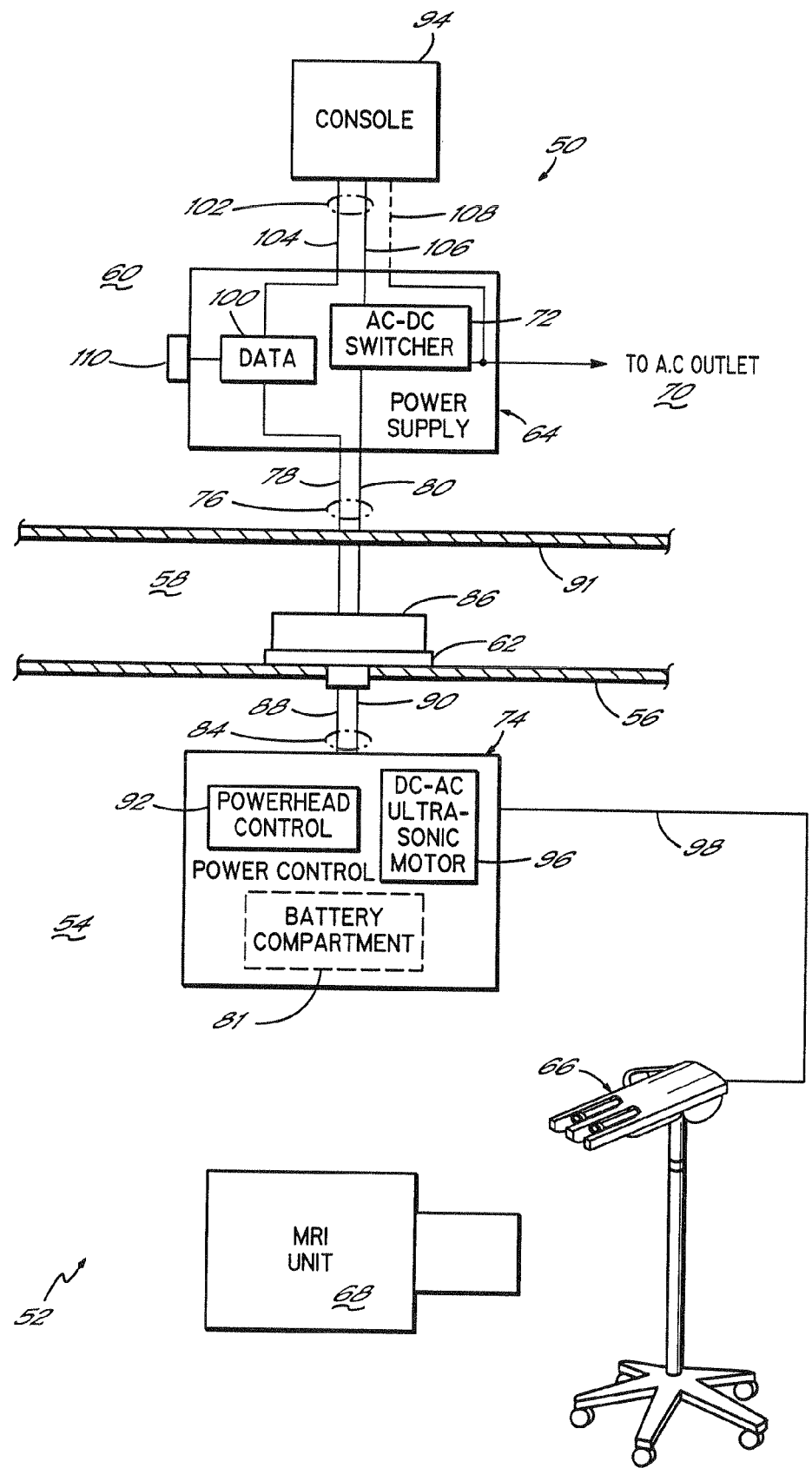
FIG. 2 is a schematic of a power injector consistent with the present invention with components installed in the magnet room directly powered by other components installed outside of the magnet room.

Turning to FIG. 2, a remotely powered MR injector system 50 consistent with the present invention is installed in an MRI suite 52 having a magnet room 54 enclosed within EMI shielded walls 56. Other portions of the MRI suite 52, depicted as an equipment room 58 and a control room 60, are electrically accessible to the magnet room 54 via a penetration panel 62 in the EMI shielded walls 56. A power supply 64 of the system 50 advantageously provides electrical power to the entire system 50, reaching portions of the system 50 within the magnet room 54 via the penetration panel 62, thereby eliminating the need for battery power to power a power head 66 near an MRI unit 68.

The power supply 64 simplifies installation in the MRI suite 52 by accessing a standard AC outlet 70 in the control room 60. In the illustrative embodiment, the power supply 64 converts standard utility AC power from the outlet 70 into several forms suitable for the other major components of the system 50 with an AC-DC switcher 72, such as a GPM225 global performance switcher available from Condor D.C. Power Supplies, Inc. of Oxnard, Calif. This AC-DC switcher 72 is suitable for use in a medical facility such as control room 60 and may be flexibly supplied from outlet power ranging from 28-264 Vac, 47-63 Hz single phase. Examples of alternative implementations of switcher 72 include the PM200 Series of AC-DC switching power supplies from International Power Sources, Inc. of Holliston, Mass.

For an existing OPTISTAR™ MR system, the power supply 64 advantageously emulates the power performance of the batteries installed into a conventional power control 74 in the magnet room 22. Specifically, a first electrical cable 76 outside of the magnet room 22 couples the power supply 64 to the penetration panel 62. The first electrical cable includes data conductors 78 suitable for electronic data signals for sensing and command signals and power conductors 80 suitable for electrical power signals for powering electronics and electro-mechanical devices (e.g., ultrasonic motors of power head 66). For instance, the power conductors 80 may be coupled to the battery compartment 81 to utilize existing electrical power wiring in the power control 74.

The first cable 76 connects to a conventional RF filter 86 at the penetration panel 62. The RF filter 86 grounds conductive shields of the first cable 76 so that induced noise on the shields is reduced at the EMI shielded wall 56. Also, the RF filter 86 attenuates RF noise on data and power conductors 76, 80 within a rejection frequency band selected to correspond to the RF frequencies used by the MRI unit 68. On the inside of the magnet room 54, the other side of the penetration panel electrically couples to a second electrical cable 84 via a free hanging D-shell connector (not shown). The other end of the second cable 84 couples to the power control 74. Like the first cable 76, the second electrical cable 84 includes data conductors 88 suitable for electronic data signals for sensing and command signals and power conductors 90 suitable for electrical power signals for powering electronics and electromechanical devices.

It will be appreciated that additional interconnections may be made, such as wall connector (not shown) in the wall 91 between the console room 60 and the equipment room 58. Similarly, instead of one cable 76, 84, 98, respectively, between major components 64, 66, 74, 94 of the system 50, a plurality of cables electrically run in parallel may be used.

The power control 74 includes power head control electronics 92 that receives feedback and any operator commands input at the power head 66. The power head control electronics 92 further provides operation status data to a touch-screen console 94 in the control room 60 for display to an operator. The power head control electronics 92 also receives commands from the console 94 and responds by activating a DC-AC ultra sonic motor drive 96 to produce a signal over a power head cable 98 to the power head 66 to actuate syringe plungers to dispense contrast media and/or saline solution.

The power supply 64 facilitates communication between the console and power control 74 by including a data link 100 that couples the first cable 76 to a console cable 102. The console cable 102 advantageously includes data conductors 104 for conducting data signals and power conductors 106 for powering the console 94. Alternatively or in addition to power conductors 106, the power supply 64 may include an interconnection between the AC power received from the AC outlet 70 to an AC outlet 108 externally mounted for a conventional electrical plug of a conventional monitor 94. The data link 100 may further include an original equipment manufacturer (OEM) data port 110 for later upgrades to the system 50.

In use, an operator of a remotely powered MR injector system 50 installs a console 94 and power supply 64 in a control room 60 of an MRI suite 52 by plugging the power supply 64 into an AC outlet 70. A console cable 102 is connected between the console 94 and the power supply 64. A power control 74 and a power head 66 are positioned within the magnet room 54. Specifically, the power head 66 is placed proximate to the MRI unit 68 and connected via power head cable 98 to the power control 74. The power control 74 is spaced away from the MR unit 68. Ideally, any ferromagnetic components of the power control 74 are not only shielded, but also oriented such that the entire power control 74 may be oriented with respect to the magnetic field from the MRI unit to minimize magnetic field interruption. Communication between the portions of the system in rooms 54, 60 is facilitated by cables 76, 84 between the power supply 64 and power control 74. In addition, cables 76, 84 include power conductors 80, 90 to remotely power the power head 66 via power control 74.

By virtue of the foregoing, an improved MR injector system 50 is operable within the demanding EMIC constraints of the MRI suite 52 without the inconvenience and additional costs of using battery power inside the magnet room 54.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. A method of operation for an MR injector system that comprises a power supply, a cable, a battery compartment, a radiofrequency filter, and a power head, the method comprising:

the power supply of the injector system receiving AC power from an AC power outlet;

the power supply converting the AC power received to DC power;

conveying DC power from the power supply through a penetration panel of an MRI suite and the cable of the injector system toward the battery compartment of the injector system;

the radio frequency filter of the injector system filtering radio frequency energy emitted during the conveying of the DC power from the power supply toward the battery compartment, and conveying the DC power from the battery compartment to the power head of the injector system.

2. The method of claim 1, wherein the battery compartment is devoid of a battery during the conveying of power from the power supply toward the battery compartment.

3. The method of claim 1, wherein the battery compartment is devoid of a battery during the conveying of power from the battery compartment to the power head.

4. The method of claim 1, further comprising a power control that comprises the battery compartment.

5. The method of claim 1, wherein the filtering occurs prior to the power being conveyed through the penetration panel.

6. The method of claim 1, wherein the filtering comprises attenuating RF noise within a rejection frequency band selected to correspond to RF frequencies used by an MRI unit.

7. The method of claim 1, further comprising:

transmitting data signals from a control panel of the injector system to a power head of the injector system.

8. The method of claim 1, further comprising:

installing a syringe containing contrast media on the power head of the injector system, and energizing the power head with power from the battery compartment to expel contrast media from the syringe.

9. An MR injector system comprising:

a power head configured to operate a syringe to dispense medical fluid from a syringe mounted thereto;

a power supply configured to receive AC power from an AC power outlet and to convert the received AC power to DC power; and a power connection configured to convey power from the power supply to the power head, the power connection comprising:

a cable;

a battery compartment toward which DC power from the power supply is conveyed via the cable and from which DC power is conveyed to the power head; and a radio frequency filter that filters radiofrequency energy, wherein the radio frequency filter attenuates RF noise within a rejection frequency band selected to correspond to RF frequencies used by an MRI unit.

10. The injector system of claim 9, wherein the radio frequency filter grounds conductive shields of the power connection.

11. The injector system of claim 9, wherein the battery compartment is devoid of a battery.

12. The injector system of claim 9, further comprising:

a control panel configured to generate data signals to control the power head; and a data connection configured to convey data signals from the control panel to the power head.

13. The injector system of claim 9, wherein the cable comprises conductive shields.

14. The injector system of claim 9, wherein the power connection comprises a second cable configured to convey power from the battery compartment to the power head.

15. The injector system of claim 9, wherein the power head comprises an ultrasonic motor.

16. The injector system of claim 9, further comprising a power control that comprises the battery compartment.

17. The injector system of claim 9, further comprising a syringe mounted to the power head.

18. The injector of claim 17, further comprising contrast media disposed within the syringe.

* * * * *